(12) United States Patent
Park et al.

(10) Patent No.: US 8,283,139 B2
(45) Date of Patent: Oct. 9, 2012

(54) METHOD OF PRODUCING XYLITOL USING HYDROLYSATE CONTAINING XYLOSE AND ARABINOSE PREPARED FROM BYPRODUCT OF TROPICAL FRUIT BIOMASS

(75) Inventors: Seung-won Park, Gyeonggi-do (KR); Joo-hang Lee, Gyeonggi-do (KR); Taek-beom Kim, Seoul (KR); Jung-hoon Kim, Seoul (KR); Seong-bo Kim, Seoul (KR); Sang-hoon Song, Incheon (KR); Kang-pyo Lee, Seoul (KR); Seung-bae Ji, Incheon (KR); Dong-hoon Lee, Gyeonggi-do (KR); Kang-deug Lee, Incheon (KR)

(73) Assignee: CJ Cheiljedang Corporation, Seoul (KR)

( * ) Notice: Subject to any disclaimer, the term of this patent is extended or adjusted under 35 U.S.C. 154(b) by 338 days.

(21) Appl. No.: 12/522,741

(22) PCT Filed: Jan. 25, 2008

(86) PCT No.: PCT/KR2008/000457
§ 371 (c)(1),
(2), (4) Date: Jul. 10, 2009

(87) PCT Pub. No.: WO2008/096971
PCT Pub. Date: Aug. 14, 2008

(65) Prior Publication Data
US 2010/0068121 A1 Mar. 18, 2010

(30) Foreign Application Priority Data

Feb. 9, 2007 (KR) .................. 10-2007-0013795
Jul. 20, 2007 (KR) .................. 10-2007-0072682

(51) Int. Cl.
*C12P 19/02* (2006.01)
*C13K 13/00* (2006.01)
(52) U.S. Cl. .................. 435/105; 127/37; 127/46.3
(58) Field of Classification Search .............. 423/445 R; 127/37, 46.3; 44/589, 605; 435/105
See application file for complete search history.

(56) References Cited

U.S. PATENT DOCUMENTS

| | | | |
|---|---|---|---|
| 3,718,560 A * | 2/1973 | Sugiyama et al. | 204/530 |
| 4,612,286 A * | 9/1986 | Sherman et al. | 435/157 |
| 4,778,531 A * | 10/1988 | Dobler et al. | 127/46.1 |
| 5,340,403 A | 8/1994 | Fields et al. | |
| 6,352,845 B1 | 3/2002 | Buchanan et al. | |
| 6,663,780 B2 | 12/2003 | Heikkila et al. | |
| 7,008,485 B2 | 3/2006 | Heikkila et al. | |
| 7,109,005 B2 | 9/2006 | Eroma et al. | |
| 2002/0153317 A1 | 10/2002 | Heikkila et al. | |
| 2006/0281913 A1 | 12/2006 | Ferreira et al. | |

FOREIGN PATENT DOCUMENTS

| | | |
|---|---|---|
| CN | 1165195 A | 11/1997 |
| CN | 1861520 A | 11/2006 |
| JP | 54-067093 | 5/1979 |
| JP | H10-192000 A | 7/1998 |
| JP | H11-313700 A | 11/1999 |
| JP | 2001-226111 * | 8/2001 |
| JP | 2006-087390 A | 4/2006 |
| KR | 10-2000-012825 A | 3/2000 |
| KR | 10-2000-038423 A | 7/2000 |
| KR | 10-2000-051095 A | 8/2000 |
| KR | 10-2000-055003 A | 9/2000 |
| KR | 10-2001-0107331 A | 12/2001 |
| KR | 10-2002-0059673 | 7/2002 |
| KR | 10-2002-0095809 A | 12/2002 |
| KR | 2004-18323 A | 3/2004 |
| KR | 10-2005-003585 A | 1/2005 |
| KR | 10-2005-0025059 A | 3/2005 |
| KR | 10-2005-0031310 A | 4/2005 |
| KR | 10-2008-0074687 | 8/2008 |
| WO | WO 02/053783 | 7/2002 |

OTHER PUBLICATIONS

Written Opinion issued Apr. 7, 2008 in PCT/KR2008/000457.
Search Report issued Apr. 7, 2008 in PCT/KR2008/000457.
Daud et al. (2000) Carbon. 38:1925-1932, "The effects of carbonization temperature on pore development in palm-shell-based activated carbon".
Daud & Ali (2004) Bioresource Technology. 93:63-69, "Comparison on pore development of activated carbon produced from palm shell and coconut shell".
Demirbas (2006) J. Anal. Appln. Pyrolysis 76:285-289, "Effect of temperature pyrolysis products from four nut shells".
Huang et al. (2005) Institute of Science and Engineering, Hainan University, Fine Chemical Industry Key Laboratory of Hainan, Hikou 570228, China 26(8):252-255, "The Choice of the Best Technology in the Xylose Solution Prepared Xylose by the Coconut Shell".
International Search Report for PCT/KR2009/006359 dated Aug. 16, 2010.
Internet publication: www.knrda.go.kr/club/club_beta/05/sub-04-main3-199.htm, (2002) "Process and use of starch" (w/ English abstract).

(Continued)

*Primary Examiner* — David M Brunsman
(74) *Attorney, Agent, or Firm* — Swanson & Bratschun, L.L.C.

(57) ABSTRACT

Disclosed is a method of producing xylitol using a hydrolysate containing xylose and arabinose prepared from byproducts of tropical fruit biomass and more precisely, a method of producing xylitol which includes the steps of producing xylose and arabinose by the pretreatment of tropical fruit biomass byproducts including coconut shell, palm shell and oil palm empty fruit bunch (OPEFB) via acid (0.2-5%) hydrolysis and an electrodialysis and an ionic purification; and producing xylitol with high yield based on repeated batch fermentation using a hydrolysate containing xylose and arabinose as a carbon source. In addition, the present invention relates to an active carbon produced by carbonization and activation of a hydrolysate remainder of a tropical fruit shell, the byproduct of xylose and arabinose production, at a certain temperature and a preparation method of the same.

5 Claims, 2 Drawing Sheets

OTHER PUBLICATIONS

Parajo et al. (1998) "Production of Carotenoids by *Phaffiarhodozyma* Growing on Media Made from Hemicellulosic Hydrolysates of *Eucalyptus globulus* Wood" Biotechnology and Bioengineering, 59(4):501-506.

Roehr (2001) "Classical and Future Applications, Wiley-VCH" Biotechnology of Ethanol, 173-173.

Shibanuma (1999) "Partial Acid Hydrolysis of Corn Fiber for the Production of L-Arabinose" J. Appl. Glycosci, 46(3):249-256.

* cited by examiner

METHOD OF PRODUCING XYLITOL USING HYDROLYSATE CONTAINING XYLOSE AND ARABINOSE PREPARED FROM BYPRODUCT OF TROPICAL FRUIT BIOMASS

RELATED APPLICATIONS

This application is a 35 U.S.C. §371 national phase application of PCT/KR2008/000457 (WO 2008/096971), filed on Jan. 25, 2008, entitled "Method of Producing Xylitol Using Hydrolysate Containing Xylose and Arabinose Prepared From Byproduct of Tropical Fruit Biomass," which application claims the benefit of Korean Patent Application Serial No. KR 10-2007-0013795, filed on Feb. 9, 2007 and Korean Patent Application Serial No. KR 10-2007-0072682, filed on Jul. 20, 2007. Each of these applications is specifically incorporated herein by reference in its entirety.

TECHNICAL FIELD

The present invention relates to a method of producing xylitol using a hydrolysate containing xylose and arabinose prepared from a byproduct of a tropical fruit biomass. More precisely, the present invention relates to a method of producing xylitol which includes the steps of producing xylose and arabinose by the pretreatment of tropical fruit biomass byproduct including coconut shell, palm shell and oil palm empty fruit bunch (OPEFB), such as an acid (0.2-5%) hydrolysis and an electrodialysis (ED) and an ionic purification; and producing xylitol with high yield based on repeated batch fermentation using the hydrolysate containing the above xylose and arabinose as a carbon source. In addition, the present invention relates to an active carbon produced by carbonization and activation of the hydrolysis remainder of the tropical fruit shell, the byproduct of xylose and arabinose production, at a certain temperature and a preparation method of the same.

BACKGROUND ART

Xylitol is industrially produced by a chemical reduction of hemicellulose hydrolysate prepared from plant materials such as birch and corncob, etc, or by a biological conversion of the hydrolysate using a microorganism. The chemical reduction, however, not only is difficult to separate and purify xylitol or xylose from other hydrolysates produced from hemicellulose and gives as low yield as 50-60% but also has risks of undergoing a reaction at high temperature and high pressure using alkali and waste problem.

One of the alternative biological methods which are expected to have high price competitiveness compared with the conventional chemical methods is the attempt to produce xylitol using a renewable resource containing a required amount of sugar based on a biological procedure. Although this method is expected to reduce production costs and enables recycling of resources, there is still a long way to go to establish a method of producing xylitol using such a renewable resource based on a biological method. Studies are undergoing to develop a highly efficient saccharification process using a fibrous biomass. But they are all focused on soft materials such as a straw and a corn stover.

Biomass is a reusable organic material extracted from energy crops and trees, agricultural products and forage crops, agricultural wastes and remnants, forestry wastes and debris, water plants, animal excrements, municipal wastes and other various wastes. It also indicates organic components of wood, plants, agricultural forestry byproducts, municipal wastes and industrial wastes which have been used as an energy source.

Among many natural fibrous biomasses, plants (leaves, stems and roots) are composed of three major components of cellulose, hemicellulose and lignin and other minor resins. From the decomposition or conversion of such components, a renewable resource, which is fibrous hydrolysate having high xylose content can be prepared. During the xylose production, arabinose can also be additionally obtained. To separate or decompose the above major three components, bonds among them have to be first disrupted before the conversion.

Up to date, xylose has been produced by the steps of acid-hydrolysis of hemicellulose existing in wood, straw or corncob, decoloration, ion purification and crystallization. The hydrolysate obtained from the acid-hydrolysis contains xylose, arabinose and a large amount of inorganic ions, so that purification process is required to eliminate such inorganic ions.

The purification of usable sugar components including xylose from the hydrolysate has been generally performed by the following processes. A neutralizing agent is added to the hydrolysate of acid-hydrolysis to adjust pH to 3.0~7.0 v to obtain a precipitate; the precipitated salt is separated by filtering; color materials are eliminated by using charcoal; then the hydrolysate proceeds to ion exchange resin tower filled with cation exchange resin, anion exchange resin and mixed resin in that order, resulting in the separation of usable ingredients including xylose from the hydrolysate.

In the above processes, all ions in the hydrolysate are attached on the ion exchange resin and acids and alkalis are passed through, resulting in the separation of ions and the recovery of the resin. The solution containing the usable sugar components purified from ion exchange resin tower proceeds to a separation tower filled with $Na^+$ type chromatography separation resin in the form of sulfated polystyrene cross-linked with divinylbenzene. As a result, the fraction with xylose in high content and the fraction having high arabinose content can be obtained. The fractionated xylose and arabinose are concentrated by Brix 60~80, followed by crystallization to give xylose crystals and arabinose crystals.

In the purification process above, precipitation is induced by adding a chemical substance that is able for form an insoluble salt with the inorganic ion. And, the precipitated salt is separated by using a filter and as a result the salt concentration is reduced. However, salt residue remaining not-filtered can form a scale during the concentration, even though it is a small amount, resulting in the decrease of productivity. According to the method using an ion exchange resin, massive ion exchange resins are required to treat such samples that have high content of total ions. And large amount of acid/alkali solution is necessarily used for the regeneration of the ion exchange resin. Accordingly, waste water containing high content of salt increases with increasing the waste water treatment costs. Therefore, an alternative technology to reduce chemicals and waste water is strongly requested.

Another exemplary purification method is ED (electrodialysis). ED is a purification method to eliminate impurities included in the reaction solution such as colloid using direct current voltage. At this time, an ion-exchange membrane is generally used.

The conventional ED had an economical limitation in industrial applicability because this method requires high energy cost and an expensive ion exchange membrane. However, since 1980s, approximately 50 ion exchange membranes have been developed by many companies including Asahi Chemical, Asahi Glass and Tokuyama Co. of Japan and Ionics and Dupont of USA, reducing high economic costs. There are also many patent applications in relation of ED ([Recovering method of organic acids] (Application No: 98-0053421), [Production methods of lysine-HCl] (Application No: 98-0011107), [Separation and purification methods for phenylalanine by electrodialysis] (Application No: 99-0001349), [Recovery method of lactic acid by electrodialysis process] (Application No: 00-0028758), [Method for purification of amino acid containing solutions by electrodialysis] (Application No: 02-7005661), etc).

In general, an organic material can be burned because of carbon (C) therein, and any substance can be used as a raw material for the production of the active carbon as long as it can be burned. Representative raw materials for the production of active carbon are wood, lignite and anthracite, etc, and active carbon is produced by carbonizing them to charcoal. The charcoal is mainly composed of carbon resulted from the incomplete oxidation during carbonization of wood, and the charcoal varies from the kind of wood and temperature of burning. The major wood materials for charcoal are exemplified by an oak, a bamboo, a broadleaf tree, a palm tree, a coconut, etc, and particularly the charcoal made by an oak has been known to have better treatment effect on water purification, cleaning, fuel and garden plants, compared with other charcoal produced from a broadleaf tree, a bamboo, a palm tree or a coconut.

The two most important processes for the production of an active carbon are the carbonization process and activation process. The carbonization process indicates the procedure in which a raw material is heated at 500~700° C., leading to dehydration and deoxidation, and then the surface oxygen is released as the forms of water, carbon monoxide and carbon dioxide, suggesting that all the volatile ingredients are eliminated and fixed carbon is left alone. The activation process indicates the oxidation reaction of carbon occurring at 800~1,000° C., in which the surface of a carbide is eroded and thereby micropore structure is developed in the carbide.

The patents regarding the production of charcoal using byproducts of tropical fruit biomass are exemplified by Korean Patent Publication No. 2002-0095809 (Coconut charcoal and manufacturing process of it), No. 2000-0055003 (Manufacturing process of yellow ocher charcoal), No. 10-2005-0003585 (Charcoal and manufacturing method thereof), No. 2000-0012825 (Manufacturing process of coconut shell charcoal briquette) and No. 10-2005-0031310 (Ignition coal using palm charcoal dust and manufacturing method thereof). As shown in the list, there are many reports regarding the method of preparing various pressing charcoals using palm charcoal dust as a major raw material, but there have been no reports on the preparation of a high value active carbon by extracting xylose from the byproducts of tropical fruit biomass to produce charcoal using the remainders.

One problem of the conventional precipitation method is the reduced productivity owing to the scale formation. Another problem is the production of lots of waste water and the high price for the waste water treatment. Precisely, the inorganic salts and organic acids included in the hydrolysate of acid-hydrolysis resulted from the acid treatment can be eliminated by using an ion exchange resin because they have electrical charge, but to eliminate such ions rich in the hydrolysate, resin regeneration is required frequently and thereby massive acid/alkali waste water is generated. And the cost for the treatment of such waste water is very high.

DISCLOSURE OF INVENTION

Technical Problem

It is an object of the present invention to provide a method for preparing the hydrolysate containing xylose and arabinose obtained by acid-hydrolysis, electrodialysis, ion purification and decoloration of a raw material, in order to efficiently use effective ingredients including xylose in the byproducts of tropical fruit biomass such as coconut shell, palm shell and OPEFB, and to provide a method for producing xylitol from the above hydrolysate via microorganism fermentation.

It is another object of the present invention to provide an active carbon produced by carbonization and activation of the hydrolysis remainder, the byproduct resulted from the above hydrolysate preparation process, and a preparation method of the same.

Technical Solution

The above objects and other objects of the present invention can be achieved by the following embodiments of the present invention.

To achieve the objects of the invention, the present invention provides a method for preparing the hydrolysate containing xylose and arabinose, comprising the steps of acid-hydrolyzing the byproducts of tropical fruit biomass such as coconut shell, palm shell and OPEFB (Oil Palm Empty Fruit Bunch); obtaining the hydrolysate containing xylose and arabinose by the above acid-hydrolysis; and separating and purifying the hydrolysate by electrodialysis.

The present invention also provides a method for preparing xylitol, comprising the steps of adapting xylitol fermenting microorganism to the hydrolysate containing xylose and arabinose; and inoculating and fermenting the microorganism in the culture medium containing the hydrolysate as a carbon source.

The present invention further provides a method for preparing an active carbon by carbonization and activation of the hydrolysis remainder of the tropical fruit shell such as coconut shell and palm shell, the byproduct of xylose and arabinose production.

The present invention is described in detail hereinafter.

The present invention provides a method for preparing the hydrolysate containing xylose and arabinose, comprising the steps of acid-hydrolyzing the byproducts of tropical fruit biomass such as coconut shell, palm shell and OPEFB (Oil Palm Empty Fruit Bunch); obtaining the hydrolysate containing xylose and arabinose by the above acid-hydrolysis; and separating and purifying the hydrolysate by electrodialysis.

The byproducts of tropical fruit biomass of the present invention, which are coconut shell, palm shell and EFB (Empty Fruit Bunch), are pulverized into 0.5~5 cm$^2$ in average surface area or 0.1~5 cm in average length, followed by drying at 40~80° C. for 12~24 hours.

Acid-hydrolysis is induced by the following steps; 100~1,000 g of 0.2~5.0% sulfuric acid solution is added to 100 g of the dried coconut shell, palm shell or OPEFB (Oil Palm Empty Fruit Bunch) to make a mixture of a solvent and the biomass for acid-hydrolysis at the ratio of 1:1~1:20; and the mixture is reacted by stirring at 100~200° C., 10~50 rpm under the reaction pressure of 0~10 kgf/cm$^2$ for 0.5~10 hours.

To recover the soluble substances dissolved in the solution after the acid-hydrolysis, the precipitate is eliminated and pH of the hydrolysate is up-regulated from 1.0~2.0 to 3.0~7.0, followed by stirring at 60~90° C. for 30~120 minutes. Sulfate ion in the hydrolysate is reacted with calcium ion to precipitate as calcium sulfate. The hydrolysate is cooled down to under 30° C. using a heat exchanger. Calcium sulfate hydrated in the reaction solution is precipitated by using the difference of solubility over temperature. The precipitated calcium sulfate is eliminated by a filter cloth. The filtered reaction solution is desalinated with conductivity of up to 1,000 μS/cm by electrodialysis.

In the above precipitation, however, non-precipitated remaining salts, even though they are a small amount, might form a scale during concentration process and reduce productivity. So, to overcome this problem, the present inventors introduced electrodialysis. According to this electrodialysis, a scale that cause a problem is not formed, so that the productivity of xylose and arabinose is increased and the total amount of ions remaining in hydrolysis is reduced with reducing the repeated numbers of resin regeneration necessary for the method using an ion exchange resin, resulting in the significant decrease of the use of acid/alkali solution. The production of xylose and arabinose via electrodialysis has advantages of reducing the amount of waste water and reducing production costs owing to the increase of productivity.

The electrodialysis apparatus preferably includes the ion exchange membrane, the electrode plate, the flow control pump and the rectifier.

The desalinated reaction solution is vacuum-concentrated with the sugar concentration of 25~45 Brix, followed by decoloration using a granular activated carbon. At this time, the decoloration is preferably performed at 79~80° C. at linear velocity (LV) of 1~3 m/hr.

The decolored reaction solution proceeds to a strong acid cation exchange resin, a weak alkali anion exchange resin and a mixed resin one after another to eliminate inorganic salts and ionic substances. As a result, the hydrolysate containing xylose as a major component, a small amount of arabinose and other monosaccharides (up to 5%) is prepared. The ion exchange membrane herein is preferably composed of a cation membrane and an anion membrane.

The present invention also provides a method for preparing xylitol, comprising the steps of adapting xylitol fermenting microorganism to the hydrolysate containing xylose and arabinose; and inoculating and fermenting the microorganism in the culture medium containing the hydrolysate as a carbon source.

The hydrolysate of the present invention is obtained by the method described hereinbefore, which is added to the microorganism culture medium for the production of xylitol after being through separate pre-treatment processes (neutralization, filtering, and purification using an ion exchange resin). The culture medium for fermentation is preferably the one that contains a complex nitrogen source such as yeast extract, malt extract and soybean cake, $KH_2PO_4$, and $MgSO_4.7H_2O$.

The xylitol fermenting microorganism of the invention is not limited to a specific one and any microorganism that is able to ferment xylitol is accepted. In this invention, *Candida tropicalis* CJ-FID and its mutants are preferably used (Korean Patent Publication No. 2005-0025059).

Figure 1:
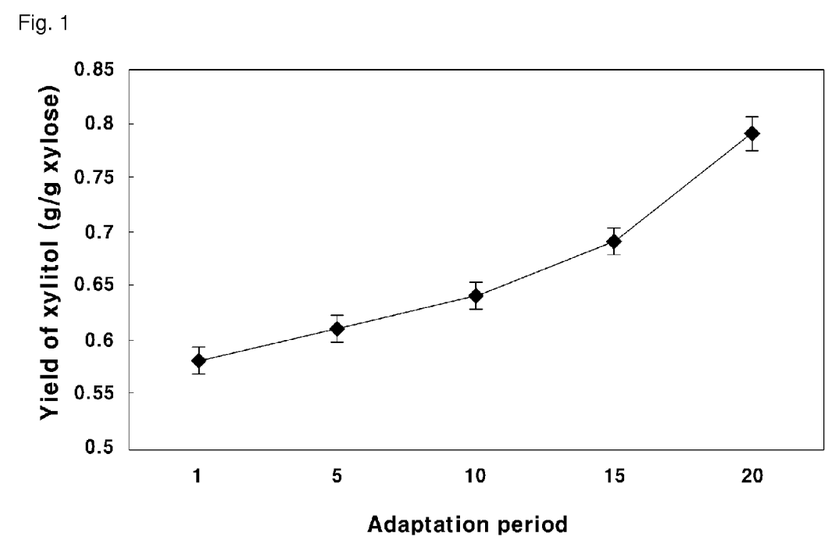
FIG. 1 is a graph illustrating the changes of conversion yield (●) over the numbers of sub-culture.

The xylitol fermenting microorganism of the invention is characteristically adapted to the hydrolysate by culturing in the medium containing the hydrolysate for a long time enough for 10~30 generation growth. It is preferred to increase conversion yield of xylitol by using the xylitol fermenting microorganism adapted to the hydrolysate by 20 sub-cultures. As shown in FIG. 1, adequate numbers of sub-culture, in order to increase the yield of xylitol by adapting the xylitol fermenting microorganism to the hydrolysate, is 20 times. Even if the sub-culture is continued farther than 20 times, the yield of xylitol is not increased. Thus, 20 times of sub-culture would be proper and economical.

The medium for sub-culture herein can be any conventional culture medium containing the hydrolysate.

Fermentation herein is carried out by batch type fermentation and repeated batch type fermentation in which a required amount of xylose hydrolysate is loaded in a single fermentor and then when the xylose is all consumed the fermentation is terminated.

According to the repeated batch type fermentation of the invention, a microorganism that can ferment xylitol is inoculated into a culture medium and cultured in a vacuumed microfiltration bioreactor. Culture solution is obtained and the medium is serially loaded in the bioreactor. The collected culture solution is separated into cells and remaining solution by using microfiltration system using vacuum pressure or a centrifuge. The microfiltration system using vacuum pressure is preferred for the efficient use of the automation system. The microfiltration system using vacuum pressure can be either separately established or equipped into the bioreactor. The separated cells are concentrated to 30~70 g/l, re-inoculated, and re-circulated in the bioreactor, followed by culture using the hydrolysate as a carbon source. Then, xylitol is recovered from the remaining culture solution separated above.

When a microorganism is used, the productivity is just 2.0~3.0 g/l-h and the cells are only possible for one-time use. But, when the microfiltration system using vacuum pressure is used, the cells are reusable without loss, no additional cost is required for washing and pre-culture process for repeated culture, compared with repeating batch type fermentation, and xylitol can be produced economically with high yield owing to the high density culture.

The present invention further provides a method for preparing an active carbon by carbonization and activation of the hydrolysis remainder such as coconut shell or palm shell, the byproducts generated from the preparation process of the hydrolysate containing xylose and arabinose resulted from the acid-hydrolysis of the byproducts of tropical fruit biomass such as coconut shell and palm shell.

Precisely, according to the method for preparing an active carbon of the invention, the hydrolysate containing xylose and arabinose is separated by acid-hydrolysis and the remaining byproducts of tropical fruit biomass such as coconut shell and palm shell are hydrolyzed and the byproducts therefrom are used as the raw material for the active carbon, which were carbonized at 500~1,000° C. for 72~168 hours and activated to prepare a gas-absorbing active carbon with high purity.

The carbon purity of the hydrolysis remainder is increased during the extraction process, the ash content is decreased. Using the hydrolysis remainder, a high quality active carbon such as a high purity gas-absorbing active carbon can be prepared due to the development of micropore production method.

To produce the gas-absorbing active carbon with high purity, the acid-hydrolysis remainders are collected, dried at 40~100° C. for 24~48 hours, and carbonized and activated at 500~1,000° C. for 72~168 hours.

The active carbon of the invention has excellent gas-absorbing capacity, compared with the conventional active carbon produced from coconut shell or palm shell not been through acid-hydrolysis (see Table 6).

BRIEF DESCRIPTION OF THE DRAWINGS

The application of the preferred embodiments of the present invention is best understood with reference to the accompanying drawings, wherein.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Xylose and Arabinose

Coconut shell, palm shell and OPEFB, the byproducts of tropical fruit biomass, were pulverized into 0.5~5 cm$^2$ in average area or 0.1~5 cm in average length, and dried at 40~80° C. for 12~24 hours.

Acid-hydrolysis was performed by the following steps; 100~1,000 g of 0.2~5.0% sulfuric acid solution was added to 100 g of the dried coconut shell, palm shell or OPEFB to make a mixture of the biomass and a solvent for acid-hydrolysis at the ratio of 1:1~1:20; and the mixture was reacted by stirring at 100~200° C., 10~50 rpm under the reaction pressure of 0~10 kgf/cm$^2$ for 0.5~10 hours. Sugar compositions according to the extraction time are shown in Table 1.

TABLE 1

| | Sugar compositions according to extraction time (%) | | | | | | | | | | | |
|---|---|---|---|---|---|---|---|---|---|---|---|---|
| | Coconut shell | | | | Palm shell | | | | OPEFB | | | |
| | Glu | Xyl | Ara | Gal | Glu | Xyl | Ara | Gal | Glu | Xyl | Ara | Gal |
| 0.5 hr | 6.4 | 87.7 | 5.9 | — | 8.8 | 88.3 | 2.9 | — | 6.7 | 88.8 | 4.5 | — |
| 1 hr | 5.6 | 89.5 | 4.9 | — | 7.4 | 89.2 | 3.4 | — | 5.9 | 87.3 | 5.8 | 1.0 |
| 3 hr | 7.9 | 85.6 | 5.5 | 1.0 | 11.9 | 83.1 | 4.1 | 0.9 | 7.9 | 85.2 | 7.4 | 1.5 |
| 6 hr | 20.1 | 71.6 | 6.8 | 1.5 | 18.4 | 74.8 | 5.6 | 1.2 | 19.6 | 70.7 | 8.4 | 1.3 |
| 10 hr | 38.9 | 53.5 | 6.3 | 1.3 | 34.4 | 58.2 | 5.7 | 1.7 | 38.9 | 49.8 | 9.5 | 1.8 |

Glu (glucose), Xyl (xylose), Ara (arabinose), Gal (galactose)

To recover the soluble substances dissolved in the solution after the acid-hydrolysis, the precipitate was eliminated and pH of the hydrolysate was up-regulated from 1.0~2.0 to 3.0~7.0, followed by stirring at 60~90° C. for 30~120 minutes. Sulfate ion in the hydrolysate was reacted with calcium ion to precipitate as calcium sulfate. The hydrolysate was cooled down to under 30° C. using a heat exchanger. Calcium sulfate hydrated in the reaction solution was precipitated by using the difference of solubility over temperature. The precipitated calcium sulfate was eliminated by a filter press (0.5/μm). The filtered reaction solution was desalinated with conductivity of up to 1,000 μS/cm by electrodialysis. The concentrations of xylose and arabinose and conductivities before and after electrodialysis were measured and shown in Table 2.

TABLE 2

| Concentrations of xylose and arabinose and conductivities before and after electrodialysis | | | | | | | | | |
|---|---|---|---|---|---|---|---|---|---|
| | Coconut shell | | | Palm shell | | | OPEFB | | |
| | Xyl (%) | Ara (%) | Cond. (μS/cm) | Xyl (%) | Ara (%) | Cond. (μS/cm) | Xyl (%) | Ara (%) | Cond. (μS/cm) |
| Before ED | 100 | 100 | 4170 | 100 | 100 | 4570 | 100 | 100 | 3930 |
| After ED | 100 | 99.9 | 917 | 100 | 99.6 | 918 | 99.5 | 99.7 | 910 |

Xyl (xylose), Ara (arabinose), Cond. (conductivity)

The desalinated reaction solution was vacuum-concentrated with the sugar concentration of 25~45 Brix, followed by decoloration using a granular activated carbon. At this time, the decoloration was preferably performed at 79~80° C. at linear velocity (LV) of 1~3 m/hr.

The decolored reaction solution proceeded to a strong acid cation exchange resin, a weak alkali anion exchange resin and a mixed resin one after another to eliminate inorganic salts and ionic substances. As a result, the hydrolysate containing xylose as a major component, a small amount of arabinose and other monosaccharides (up to 5%) was obtained.

The hydrolysate containing useful sugars proceeded to a separation tower filled with Na$^+$ type chromatography separation resin in the form of sulfated polystyrene in which divinylbenzene is cross-linked. As a result, the fraction having high xylose content and the fraction having high arabinose content were obtained. The fractionated xylose and arabinose were concentrated by Brix 60~80, followed by crystallization to obtain xylose crystals and arabinose crystals. The yields and purity of the obtained xylose and arabinose are shown in Table 3.

EXAMPLE 2

Preparation of Xylose and Arabinose (Using Different Hydrolase)

An experiment was performed by the same manner as described in example 1 except that the acid treatment was performed with 0.2-5.0% HCl solution instead of 0.2 5.0% sulfuric acid solution. The yields and purity of the obtained xylose and arabinose are shown in Table 3.

EXAMPLE 3

Preparation of Xylose and Arabinose (Using Different Hydrolase)

An experiment was performed by the same manner as described in example 1 except that the acid treatment was performed with 0.2-5.0% oxalic acid solution instead of 0.2-5.0% sulfuric acid solution. The yields and purity of the obtained xylose and arabinose are shown in Table 3.

COMPARATIVE EXAMPLE 1

Preparation of Xylose and Arabinose (Using Different Hydrolase)

An experiment was performed by the same manner as described in example 1 except that alkali treatment was performed by 0.2-5.0% sodium hydroxide solution instead of acid treatment with 0.2-5.0% sulfuric acid solution and neutralization was induced by using HCl until pH reached 5.0-70. The yields and purity of the obtained xylose and arabinose are shown in Table 3.

TABLE 3

Yields and purity of the obtained xylose and arabinose (%)

| | Coconut shell | | | | Palm shell | | | | OPEFB | | | |
|---|---|---|---|---|---|---|---|---|---|---|---|---|
| | Xylose | | Arabinose | | Xylose | | Arabinose | | Xylose | | Arabinose | |
| | Yield | Purity | Yield | Purity | Yield | Purity | Yield | Purity | Yield | Purity | Yield | Purity |
| Example 1 | 70.4 | 99.5 | 71.6 | 98.3 | 68.4 | 98.9 | 66.6 | 98.9 | 71.7 | 99.2 | 68.4 | 98.7 |
| Example 2 | 68.8 | 98.4 | 71.7 | 97.2 | 69.8 | 98.8 | 68.7 | 98.4 | 70.5 | 99.5 | 69.5 | 98.7 |
| Example 3 | 70.2 | 98.9 | 69.3 | 98.3 | 70.6 | 98.3 | 66.9 | 98.2 | 68.4 | 99.3 | 67.8 | 99.0 |
| Comparative Example 1 | 69.6 | 98.9 | 69.8 | 98.8 | 70.6 | 98.1 | 65.2 | 98.6 | 67.2 | 98.4 | 70.1 | 97.6 |

EXAMPLE 4

Sugar Compositions of the Hydrolysates Containing Monosaccharides, Xylose and Arabinose The sugar compositions of the hydrolysates containing monosaccharides, xylose and arabinose obtained in examples 1-3 and comparative example 1 were investigated and the results are shown in Table 4

TABLE 4

Sugar compositions of the hydrolysates containing monosaccharides, xylose and arabinose

| | | Xylose | Arabinose | Glucose | Galactose | Others |
|---|---|---|---|---|---|---|
| Example 1 | Coconut shell | 90.2 | 8.4 | 1.2 | 0.2 | — |
| | Palm shell | 90.0 | 7.9 | 2.1 | — | — |
| | OPEFB | 84.3 | 9.6 | 4.1 | 1.5 | 0.5 |
| Example 2 | Coconut shell | 86.6 | 7.3 | 4.5 | 1.2 | 0.4 |
| | Palm shell | 85.9 | 8.1 | 5.3 | 0.7 | — |
| | OPEFB | 88.4 | 6.9 | 3.7 | 1.0 | — |
| Example 3 | Coconut shell | 90.8 | 4.4 | 2.4 | 1.5 | 0.9 |
| | Palm shell | 91.8 | 5.1 | 2.9 | 0.2 | — |
| | OPEFB | 91.4 | 4.9 | 3.1 | 0.6 | — |
| Comparative Example 1 | Coconut shell | 83.6 | 5.0 | 7.8 | 2.1 | 1.5 |
| | Palm shell | 85.7 | 4.8 | 7.5 | 2.0 | — |
| | OPEFB | 89.3 | 4.8 | 5.9 | — | — |

From the above results, it was confirmed that xylose crystals with at least 85% yield and 98% purity and arabinose crystals with at least 80% yield and 98% purity were produced by desalination using an ion exchange resin and crystallization according to the method of example 1.

EXAMPLE 5

Components and Contents of the Hydrolysis Remainders After Carbonization

The hydrolysis remainders, the byproducts resulted from the production of xylose and arabinose in examples 1-3 and comparative example 1 were dried at 40-100° C. for 24-48 hours, followed by carbonization at 500-700° C. for 72-168 hours (for 10 kg of the remainder) and then the components and contents were examined. Coconut shell and palm shell without acid-hydrolysis were used for the control and the components and contents of the control were also examined and shown in Table 5. As shown in Table 5, the carbon yield and fixed carbon were increased in experimental groups, compared with the control, but the ash content was reduced.

TABLE 5

Components and contents of the hydrolysis remainders after carbonization

|  |  | Control | Example 1 | Example 2 | Example 3 | Comparative Example 1 |
|---|---|---|---|---|---|---|
| Carbon yield (%) | Coconut shell | 27.7 | 29.5 | 29.0 | 28.1 | 28.9 |
|  | Palm shell | 25.8 | 27.2 | 26.9 | 27.0 | 26.8 |
| Volatile component (%) | Coconut shell | 9.3 | 5.2 | 5.9 | 6.4 | 5.5 |
|  | Palm shell | 8.7 | 4.5 | 5.3 | 4.9 | 6.0 |
| Ash (%) | Coconut shell | 1.1 | 0.4 | 0.4 | 0.5 | 0.4 |
|  | Palm shell | 1.3 | 0.6 | 0.5 | 0.5 | 0.6 |
| Fixed carbon (%) | Coconut shell | 89.6 | 94.4 | 90.4 | 92.8 | 93.5 |
|  | Palm shell | 86.5 | 94.2 | 93.7 | 94.0 | 93.8 |

EXAMPLE 6

Components and Contents of the Hydrolysis Remainders After Carbonization and Activation After carbonization of the hydrolysis remainders, which were the byproducts generated from the production of xylose and arabinose in Example 5, carbon was oxidized at 800-1,000° C. to induce surface erosion and to form a micropore structure. An active carbon was produced using coconut shell and palm shell which had not been through the acid-hydrolysis. And an active carbon prepared by gas (vapor, carbon dioxide, air, etc) activation was used as a control. Then the components and contents were examined. The results are shown in Table 6. As shown in Table 6, the active carbon prepared from the hydrolysis remainder of coconut shell and palm shell, the byproducts of tropical fruit biomass, exhibited excellent gas absorption, compared with the control.

TABLE 6

Components and contents of the hydrolysis remainders after carbonization and activation

|  |  | Control | Example 1 | Example 2 | Example 3 | Comparative Example 1 |
|---|---|---|---|---|---|---|
| Activation yield (%) | Coconut shell | 55.9 | 54.7 | 54.3 | 53.8 | 53.9 |
|  | Palm shell | 52.9 | 53.0 | 52.2 | 51.5 | 53.0 |
| Gas absorption | Coconut shell | 100 | 127 | 123 | 125 | 125 |
|  | Palm shell | 100 | 125 | 123 | 120 | 123 |
| General absorption | Coconut shell | 100 | 100 | 100 | 100 | 100 |
|  | Palm shell | 100 | 100 | 100 | 100 | 100 |
| Iodine absorption (mg/g) | Coconut shell | 1400 | 1430 | 1429 | 1423 | 1427 |
|  | Palm shell | 1390 | 1407 | 1398 | 1400 | 1403 |
| Methylene blue decoloration (mg/g) | Coconut shell | 230 | 230 | 227 | 229 | 225 |
|  | Palm shell | 228 | 226 | 228 | 226 | 226 |
| pH | Coconut shell | 10.5 | 9.7 | 9.8 | 9.9 | 9.9 |
|  | Palm shell | 10.3 | 9.9 | 10.1 | 9.9 | 9.8 |
| Hardness (%) | Coconut shell | 98.8 | 96.0 | 95.6 | 95.7 | 95.9 |
|  | Palm shell | 98.0 | 95.7 | 95.1 | 94.9 | 95.5 |

EXAMPLE 7

Batch Type Fermentation Using the Hydrolysate Containing 200 g/L of Xylose

The hydrolysate contains furfural, 5-hydroxymethyl (HMF), acetate, hydroxybenzaldehyde (HBA) and vanillin having a microorganism growth inhibiting activity. Up to date, the best xylose conversion rate was 58%. To enhance the growth of a microorganism and to improve the yield of xylitol, the present inventors adapted the xylitol fermenting microorganism through 20 times of sub-culture on the solid medium comprising the hydrolysate containing 20% of xylose as a carbon source.

According to the above method, the yield of xylitol was increased up to 80% (FIG. 1). FIG. 1 illustrates that the yield of xylitol was increased by adapting the microorganism to the inhibitor using the solid medium comprising the hydrolysate containing a microorganism growth inhibiting component as a carbon source.

First, a preculture medium comprising 20 g/L of glucose and 5 g/L of yeast extract was prepared. *Candida tropicalis* CJ FID was inoculated into a 250 ml flask containing 50 ml of the medium, followed by preculture at 30° C. with 240 rpm for 10 hours.

Figure 2:
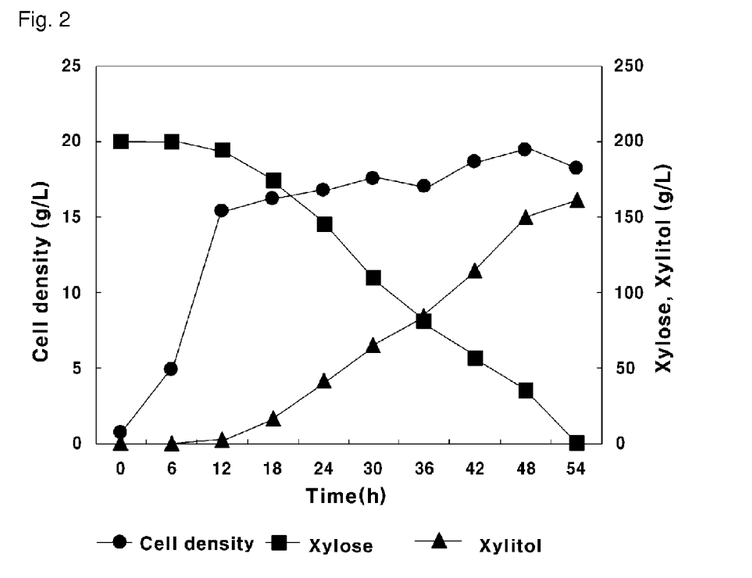
FIG. 2 is a graph illustrating the changes of cell density (●), xylose (■) and xylitol (▲) concentrations over the fermentation time according to batch type fermentation.
Figure 3:
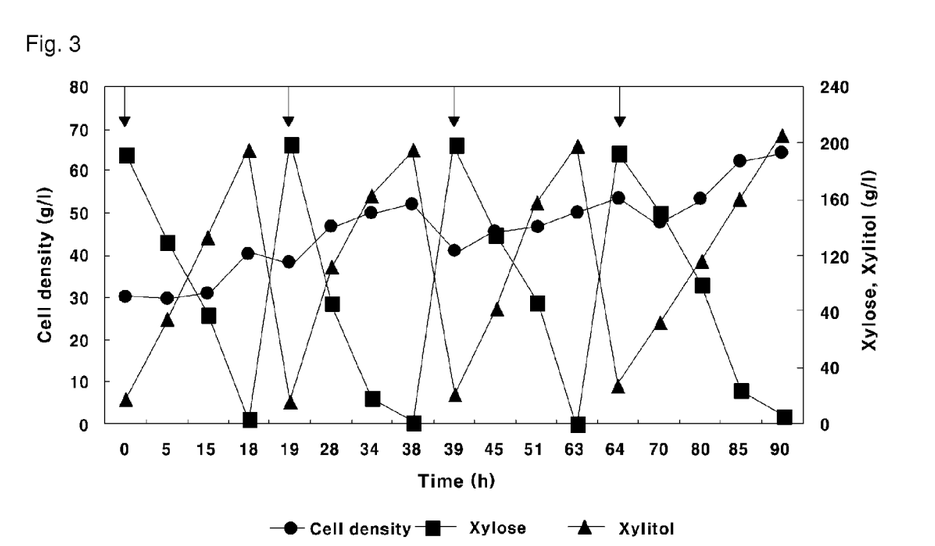
FIG. 3 is a graph illustrating the changes of cell density (●), xylose (■) and xylitol (▲) concentrations over fermentation time according to repeated batch type fermentation.

Then, a main culture medium comprising the hydrolysate containing 200 g/L of xylose, 5 g/L of yeast extract, 5 g/L urea, 5 g/L $KH_2PO_4$, and $MgSO_4H_2O$ was prepared. 2 L of the main culture medium was added into a 5 L fermentor, to which the microorganism was inoculated. The microorganism was shaking-cultured at 30° C. for 24 hours (500-300 rpm, 1.0 vvm, pH 5.0). The changes of cell density (●), xylose (■) and xylitol (▲) concentrations over the fermentation time are shown in FIG. 2.

The yield of xylitol produced by the above method and the yield of xylitol produced from the purified xylitol powder were compared and the result is shown in Table 7. As shown in Table 7, the obtained xylitol concentration was 161 g/L, cell concentration was 16.5 g/L and the yield of xylitol was 80%. In the meantime, when the purified xylitol powder was used for the production of xylitol, the yield was slightly decreased and the production time was prolonged. When the hydrolysate was used instead of the purified xylose (same microorganism was used), purification process can be omitted and thus xylitol can be prepared much more economically.

TABLE 7

|  | Xylose (g l$^{-1}$) | Cell amount (g l$^{-1}$) | Xylitol (g l$^{-1}$) | $m_{max}^a$ (h$^{-1}$) | $Q_p^b$ (gl$^{-1}$h$^{-1}$) | $Y_{p/s}^c$ (g g$^{-1}$) | Time (h) |
|---|---|---|---|---|---|---|---|
| Xylose powder | 200 | 28.4 | 166 | 0.32 | 3.53 | 0.83 | 47 |
| Xylose hydrolysate | 200 | 16.5 | 161 | 0.28 | 2.98 | 0.80 | 54 |

$^a$Maximum specific growth rate
$^b$Volumetric productivity of xylitol
$^c$Xylitol yield from xylose

EXAMPLE 8

Production of Xylitol by Repeated Batch Type Fermentation

The microorganism was cultured in the same medium as the one used in example 7 in a bioreactor. Just before xylose was all consumed, the culture solution where the reaction was terminated was transferred to microfiltration system using vacuum pressure attached to the bioreactor. The cells and the remaining reaction solution were separated and the isolated cells were concentrated. The concentrated cells were cultured in a bioreactor supplemented with 2 L of a fresh medium. The culture conditions were same as described in Example 8.

322 g of xylitol was produced from the first 2 L of culture solution which was not filtered by the microfiltration system (productivity: 2.98 g/l-h, xylitol yield from xylose: 80%). In the mean time, 1,415 g of xylitol was produced from the 8 L of the next culture solution filtered by the microfiltration system (productivity: 7.86 g/l-h, xylitol yield from xylose: 88.4%). The changes of cell density (▲), xylose (■) and xylitol (▲) concentrations over the fermentation time are shown in FIG. 2.

Industrial Applicability

In the present invention, the inventors confirmed that xylose and arabinose, the functional sugars, could be efficiently prepared from tropical fruit shell biomass by electrodialysis. The inventors also confirmed that xylitol could also be prepared repeatedly with high yield from the xylose solution by the steps of preparing hydrolysate containing xylose and arabinose; culturing a microorganism using the hydrolysate as a carbon source; concentrating the cells by a vacuum microfiltration bioreactor; reusing the concentrated cells to prepare xylitol. In addition, the inventors also confirmed that high quality carbide could be prepared by carbonizing and activating the hydrolysis remainder produced during the production of xylose and arabinose and thereby waste treatment would be less difficult and waste treatment cost could be lowered.

Therefore, according to the present invention, xylose and arabinose and further xylitol, the competitive high value functional sugars, can be efficiently produced by using inexpensive biomass.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method of preparing xylitol comprising the following steps:
    acid-hydrolyzing a byproduct of tropical fruit biomass;
    obtaining a hydrolysate containing xylose and arabinose by the acid-hydrolysis;
    separating and purifying the hydrolysate by precipitation, electrodialysis and ion exchange in sequential order;
    adapting a xylitol fermenting microorganism to the hydrolysate; and
    inoculating and fermenting the microorganism in a culture medium containing the hydrolysate as a carbon source.

2. The method for preparing xylitol according to claim 1, wherein the byproduct of tropical fruit biomass is coconut shell, palm shell or oil palm empty fruit bunch.

3. The method for preparing xylitol according to claim 1, wherein the acid-hydrolysis is performed at the acid concentration of 0.2-5%, at the temperature of 100 to 200° C. for 30 minutes to 10 hours.

4. The method for preparing xylitol according to claim 1, wherein the electrodialysis is carried out is using an electrodialysis apparatus composing of an ion exchange membrane, an electrode plate, a flow control pump and a rectifier.

5. The method for preparing xylitol according to claim 4, wherein the ion exchange membrane is composed of a cation membrane and an anion membrane.

* * * * *